(12) United States Patent
Dominguez

(10) Patent No.: US 6,526,978 B2
(45) Date of Patent: Mar. 4, 2003

(54) ENDOTRACHEAL TUBE HOLDER

(76) Inventor: Steven Dominguez, 19 Bridington, Laguna Niguel, CA (US) 92677

( * ) Notice: Subject to any disclaimer, the term of this patent is extended or adjusted under 35 U.S.C. 154(b) by 0 days.

(21) Appl. No.: 09/883,524

(22) Filed: Jun. 19, 2001

(65) Prior Publication Data

US 2002/0189614 A1 Dec. 19, 2002

(51) Int. Cl.$^7$ .............................................. A61M 16/00
(52) U.S. Cl. ............................ 128/207.14; 128/207.17; 128/DIG. 26
(58) Field of Search ....................... 128/207.11, 207.14, 128/207.17, 200.26, DIG. 26, 912

(56) References Cited

U.S. PATENT DOCUMENTS

| | | | | | |
|---|---|---|---|---|---|
| 434,501 | A | * | 8/1890 | Redhage | 128/861 |
| 4,744,358 | A | * | 5/1988 | McGinnis | 128/207.17 |
| 5,345,931 | A | * | 9/1994 | Battaglia, Jr. | 128/207.17 |
| 5,437,273 | A | * | 8/1995 | Bates et al. | 128/207.14 |
| 5,438,979 | A | * | 8/1995 | Johnson et al. | 128/207.18 |
| 5,490,504 | A | | 2/1996 | Vrona et al. | |
| 5,513,633 | A | * | 5/1996 | Islava | 128/207.14 |
| 5,520,174 | A | * | 5/1996 | Evans et al. | 128/207.14 |
| 5,551,421 | A | * | 9/1996 | Noureldin et al. | 128/207.17 |
| 5,638,814 | A | * | 6/1997 | Byrd | 128/207.17 |
| 5,803,079 | A | * | 9/1998 | Rogers et al. | 128/200.26 |
| 5,806,516 | A | | 9/1998 | Beattie | |
| 5,829,430 | A | | 11/1998 | Islava | |
| 5,868,132 | A | | 2/1999 | Winthrop et al. | |
| 5,894,840 | A | | 4/1999 | King | |
| 5,941,246 | A | | 8/1999 | Roopchand | |
| 5,996,581 | A | | 12/1999 | Duch | |
| 6,029,668 | A | | 2/2000 | Freed | |
| 6,050,263 | A | | 4/2000 | Choksi et al. | |
| 6,067,985 | A | | 5/2000 | Islava | |
| 6,105,577 | A | | 8/2000 | Varner | |
| D434,496 | S | | 11/2000 | Choksi et al. | |

* cited by examiner

Primary Examiner—William E. Tapolcai
Assistant Examiner—Mohammad M. Ali

(57) ABSTRACT

An endotracheal tube-holder for positioning a tube within a patient's trachea that includes a chin piece shaped to the curvature of the patient's chin and a pair of straps attached to openings in the chin piece for securing the tube-holder in place on the patient. An extension is attached to the chin piece extending perpendicular to and away from the patient's face. The extension includes a vertical member located at the end of the extension opposite the patient and at a fixed distance from the lips of the patient. The vertical member is split into two parts which have mating surfaces shaped for receiving and holding the endotracheal tube.

18 Claims, 2 Drawing Sheets

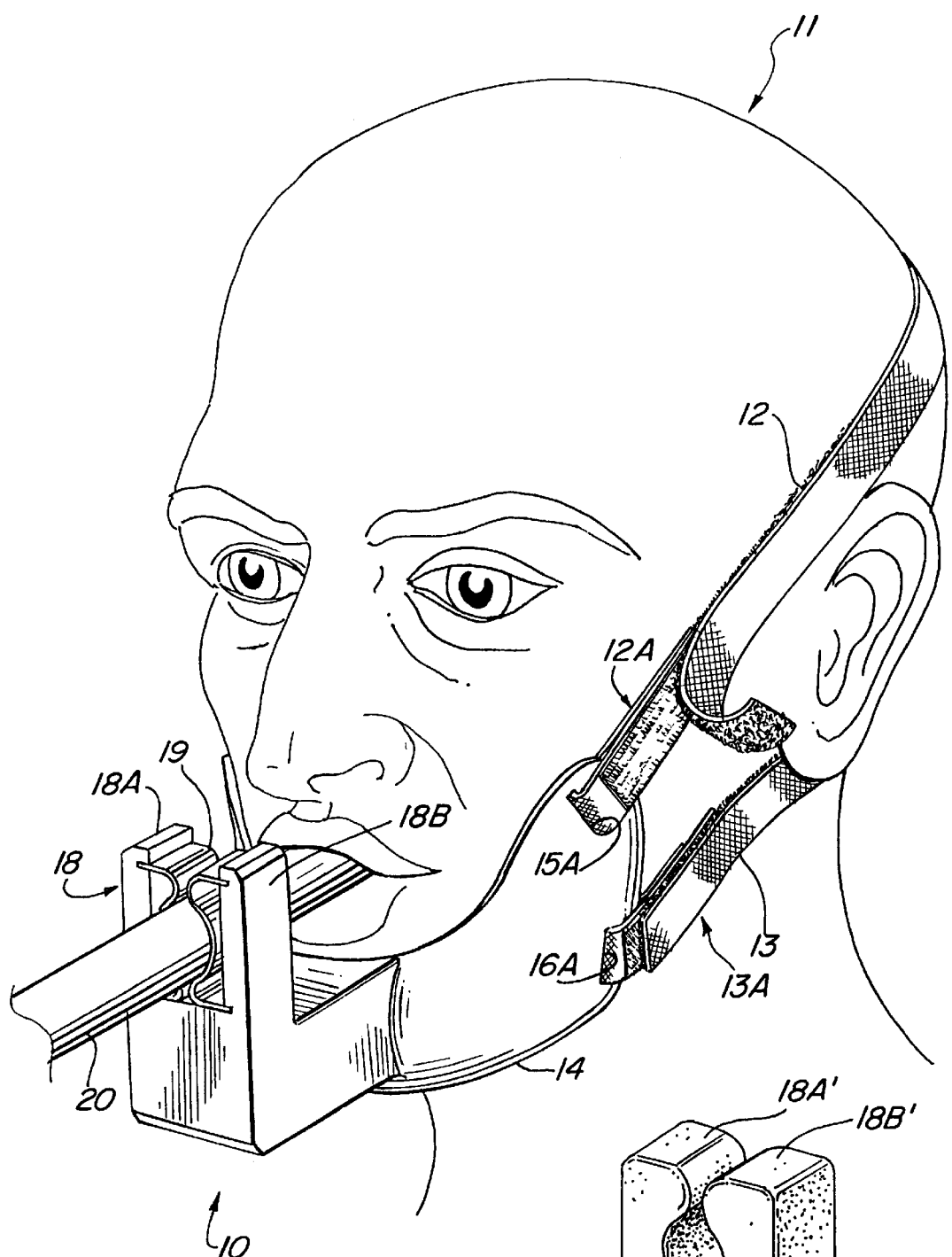
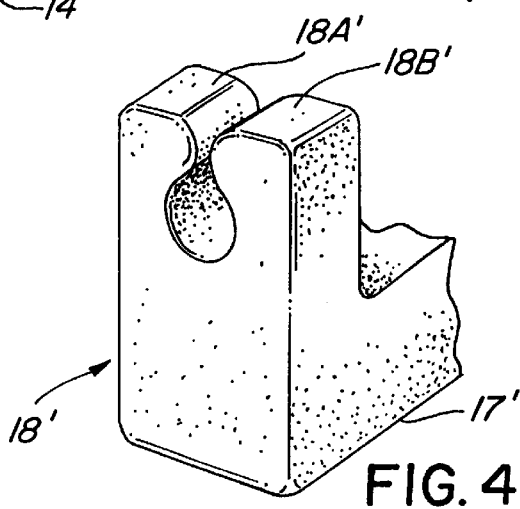
FIG. 1
FIG. 4

ENDOTRACHEAL TUBE HOLDER

BACKGROUND OF THE INVENTION

1. Field of the Invention

The present invention relates generally to endotracheal tube holders and more particularly to an improved holding device for the endotracheal tube in an adjustable position with respect to a patient's mouth.

2. Description of Related Art

Endotracheal tube devices are used under several conditions such as in the ventilation of a patient while under anesthesia, resuscitation as well as during critical care that commonly arises in the hospital and during the time when a patient is being transported.

As is well known in the art, various problems and difficulties are encountered in providing suitable means for securing an endotracheal tube in a simple and positive manner to a tube holding device that is generally part of a mouthpiece of the faceplate assembly.

Many types of securing arrangements have been used in the prior art, which very often included simply mounting the tube in place with adhesive tape that was applied to the tube and several areas of the patient's face. Some endotracheal tubes were mounted in a faceplate that included a bite block whereby the patient was required to grip the block with their teeth. However, other prior art tube holders have included various ways for securing the endotracheal tube to the faceplate of the tube holder.

U.S. Pat. No. 5,490,504 teaches an endotracheal tube attachment device in which a flexible track strip is secured across the upper lip and adjacent cheek area of a patient by means of an adhesive. Such an adhesive in intimate contact with a patient's skin for a prolonged period of time irritates the skin and often results in a breakdown of the skin tissue. To properly provide long term care of patients, depending upon an endotracheal tube, it is necessary to clean the mouth often, e.g. every 2 to 4 hours, to prevent or inhibit the development of oral bacteria. The teachings of this prior art (i.e., the '504 patent) would not appear to be conducive to such cleaning practices because the adhesive would become wet by secretion, thereby providing a further irritant to the skin. Furthermore, the tube attachment device disclosed in the '504 patent is not useable, as a practical matter, with patients that normally wear dentures since in the absence of such dentures, there is inadequate support for the track strip.

Therefore, a need exists for an endotracheal tube holder suitable for long-term use that overcomes the problems with the prior art.

SUMMARY OF THE INVENTION

An object of the present invention is to provide a tube holder that is simple to construct and simple to use, while being inexpensive to manufacture.

Another object of the present invention is to provide an endotracheal tube holder that avoids damage to a patient's skin and allows cleaning of the mouth and suctioning of the oral-pharyngeal cavity without removal of the tube.

Yet another object of this invention is to provide an endotracheal tube holder that is adjustable to a variety of shapes and sizes of patient's heads.

Still another object of the present invention is to provide an endotracheal tube holder that properly aligns and secures the tube with the patient's mouth.

Another object of the present invention is to provide an endotracheal tube holder that allows the cleaning of a patient's mouth without removing the holder.

Another object of the present invention is that the endotracheal tube holder may be quickly and safely removed in the case of significant contamination (i.e., vomitus) and a new endotracheal tube holder quickly and easily reapplied with precision and without compromising the patient's airway or otherwise necessitating reintubation.

These and other objects, which will become apparent as the invention is described in detail below, are provided by an endotracheal tube-holder for positioning a tube within a patient's trachea that includes a chin piece shaped to the curvature of the patient's chin and a pair of straps attached to openings in the chin piece for securing the tube-holder in place on the patient. An extension is attached to the chin piece extending perpendicular to and away from the patient's face. The extension includes a vertical member located at the end of the extension opposite the patient and at a fixed distance from the lips of the patient. The vertical member is split into two parts which have mating surfaces shaped for receiving and holding the endotracheal tube.

Still other objects, features and advantages of the present invention will become readily apparent to those skilled in the art from the following detailed description, wherein is shown and described only the preferred embodiment of the invention, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive, and what is intended to be protected by Letters Patent is set forth in the appended claims. The present invention will become apparent when taken in conjunction with the following description and attached drawings, wherein like characters indicate like parts, and which drawings form a part of this application.

BRIEF DESCRIPTION OF THE DRAWINGS

The general purpose of this invention, as well as a preferred mode of use, its objects and advantages will best be understood by reference to the following detailed description of an illustrative embodiment with reference to the accompanying drawings in which like reference numerals designate like parts throughout the figures thereof, and wherein:

FIG. 1 illustrates the tube holder according to the present invention as attached to a patient.

FIG. 4 is an alternate embodiment of the vertical member for holding the endotracheal tube.

DETAILED DESCRIPTION OF THE PREFERRED EMBODIMENTS

Figure 2:
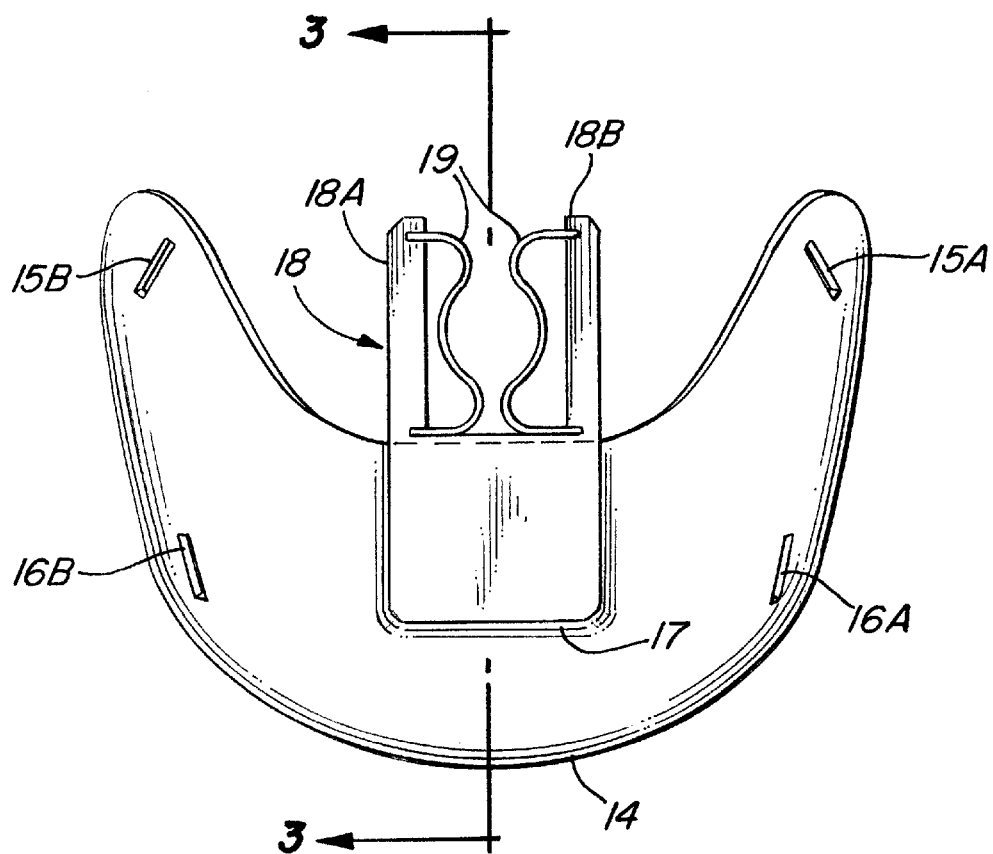
FIG. 2 illustrates a front elevation view of the tube holder according to the present invention.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a new and improved endotracheal tube holder that overcomes many of the problems associated with the prior art.

Referring now to the drawings and FIG. 1 in particular, the tube holder 10 according to the present invention is shown attached to a patient 11. The tube holder 10 is secured to the patient's head by a pair of straps 12 and 13, which are secured by Velcro connections 12A and 13A, respectively. The straps 12 and 13 grasp a chin piece 14 by loops through openings 15A and 16A in the chin piece 14. Openings 15B and 16B (not shown in FIG. 1) are on the opposite side of the chin piece 14.

The chin piece 14 includes an extension 17 that extends perpendicular to and away from the patient's chin. At the end of the chin piece 14, opposite the patient, a tube support is formed by a right angle member 18 of the extension 17. The member 18 is split into two sides 18A and 18B, and between these two sides is attached a clip 19 for holding a tube 20.

It is important to the present invention that the vertical member 18 be located away from the patient's mouth so that a medical-care attendant can clean the patient's a mouth without removing the tube 20. I have found that an optimal distance between the patient's lips and the inside of the vertical member 18 should be approximately 2 to 4 centimeters. If it is located less than 2 centimeters from the patient's lips, then there may not be enough room for an attendant to clean the patient's mouth. On the other hand, if it is located more than 4 centimeters, then the holder can become too unstable.

Referring now to FIG. 2, a front elevation view of the tube holder according to the present invention is shown. The same reference numbers are used in this FIG. 2 that were used in FIG. 1. Accordingly, the extension 17 and the right-angle member 18 are clearly shown. As stated hereinabove, the member 18 is split into two sides ISA and 18B, and between these two sides is attached clip 19 for holding the tube 20 (not shown in FIG. 2). I have found that a spring or a rachet will work for the clip 19. However, a preferred embodiment is to form the sides 18A and 18B out of flexible polymered foam or plastic material and to shape the tube holder clip 19 as shown in FIG. 4. Accordingly, a slight flexing of the sides 18A and 18B allows for greater tube stability after the insertion of the tube 20 into the clip 19.

Figure 3:
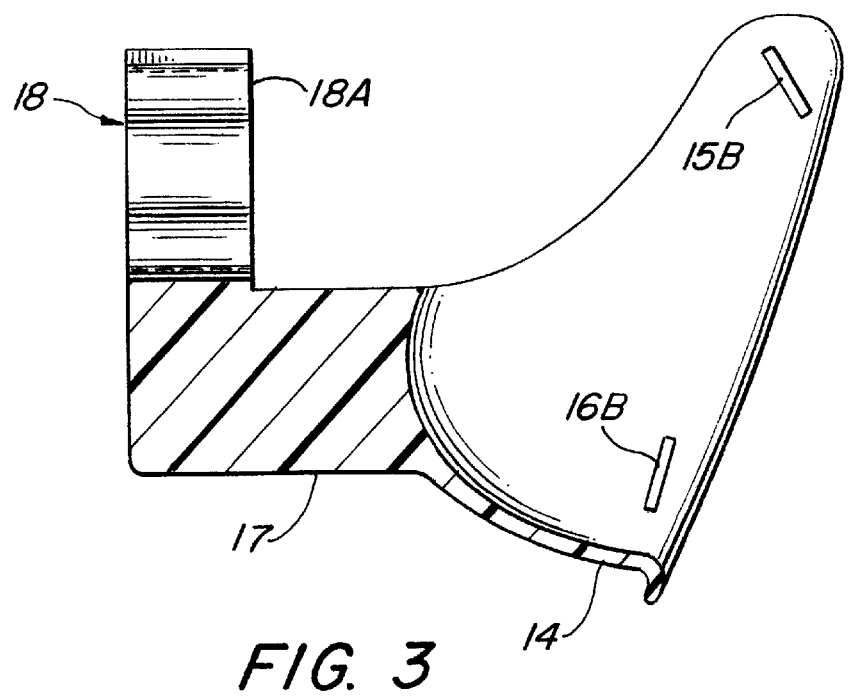
FIG. 3 is a cross-sectional view of the tube holder as depicted by the sectional lines 3—3 shown in FIG. 2.

Referring now to FIG. 3, a cross-sectional view of the chin piece 14 according to the present invention is shown. This cross-sectional view is taken along the section line 3—3 shown in FIG. 2. Again, like reference numbers are used in this Figure as well. The openings 15B and 16B for securing the straps 12 and 13 are shown in this Figure.

While the invention has been particularly shown and de therein without departing from the spirit and scope of the invention.

Those skilled in the art will appreciate that various adaptations and modifications of the just-described preferred embodiments can be configured without departing from the scope and spirit of the invention. Therefore, it is to be understood that within the scope of the appended claims, the invention may be practiced other than as specifically described herein.

What is claimed is:

1. An endotracheal tube-holder for positioning a tube within a patient's trachea comprising:
    a. a chin piece shaped to the curvature of the patient's chin along the face and underneath the chin and jaw line, locating the chin piece on the face;
    b. a pair of straps attached to openings in the chin piece for securing the chin piece in place on the patient;
    c. an extension attached to the chin piece extending perpendicular to and away from the patient's face, the extension including a vertical member located at the end of the extension opposite the patient and at a fixed distance from the lips of the patient; and,
    d. the vertical member being split into two parts with the parts shaped for receiving and holding the endotracheal tube.

2. The tube holder of claim 1 wherein said pair of straps further comprise Velcro fasteners.

3. The tube holder of claim 1 wherein the vertical member is made of foam.

4. The tube holder of claim 1 wherein the vertical member is made of plastic.

5. The tube holder of claim 1 further comprising a spring clip inserted between the two parts of the vertical member for holding the endotracheal tube.

6. The tube holder of claim 1 wherein the vertical member is located approximately 2 to 4 centimeters from the lips of the patient.

7. An endotracheal tube-holder for positioning a tube within a patient's trachea comprising:
    a. a chin piece shaped to the curvature of the patient's chin along the face and underneath the chin and jaw line, capturing the chin;
    b. means attached to the chin piece for securing the tube-holder in place on the patient;
    c. tube holding means attached to the chin piece extending perpendicular to and away from the patient's face, said tube holding means including a vertical member located at the end thereof opposite the patient and at a fixed distance from the lips of the patient; and
    d. the vertical member shaped for receiving and holding the endotracheal tube.

8. The endotracheal tube-holder of claim 7 wherein the vertical member is formed of flexible foam.

9. The endotracheal tube-holder of claim 7 wherein the vertical member is formed of plastic.

10. The endotracheal tube-holder of claim 7 further comprising a spring clip in the vertical member for holding the endotracheal tube.

11. The endotracheal tube-holder of claim 7 wherein the vertical member is located approximately 2 to 4 centimeters from the lips of the patient.

12. An endotracheal tube stabilizer comprising:
    a. a chin piece shaped to the curvature of a patient's chin along the face and underneath the chin and jaw line, locating the chin piece on the face with respect to the patient's chin;
    b. a pair of straps attached to the chin piece for securing the chin piece in place on the patient;
    c. a tube holder attached to the chin piece and extending perpendicular to and away from the patient's face, the tube holder including a vertical member located at the end thereof opposite the patient and at a fixed distance from the lips of the patient; and,
    d. the vertical member shaped for receiving and holding the endotracheal tube.

13. An endotracheal tube stabilizer as in claim 12 wherein the vertical member is located approximately 2 to 4 centimeters from the lips of the patient.

14. An endotracheal tube stabilizer as in claim 12 wherein said pair of straps are adjustably attached by means of Velcro fasteners.

15. An endotracheal tube stabilizer as in claim 12 wherein said vertical member is made of flexible foam.

16. An endotracheal tube stabilizer as in claim 12 wherein said vertical member is made of plastic.

17. An endotracheal tube stabilizer as in claim 12 wherein said vertical member includes a clip shaped for securing said endotracheal tube thereto.

18. An endotracheal tube stabilizer as in claim 12 wherein said chin piece is made of soft clear plastic.

* * * * *